US010765682B2

(12) United States Patent
Beeharry et al.

(10) Patent No.: US 10,765,682 B2
(45) Date of Patent: Sep. 8, 2020

(54) APILIMOD FOR USE IN THE TREATMENT OF MELANOMA

(71) Applicant: LAM Therapeutics, Inc., Guilford, CT (US)

(72) Inventors: Neil Beeharry, Guilford, CT (US); Sophia Gayle, East Haven, CT (US); Sean Landrette, Meriden, CT (US); Paul Beckett, Yorktown Heights, NY (US); Chris Conrad, Guilford, CT (US); Tian Xu, Guilford, CT (US); Jonathan M. Rothberg, Guilford, CT (US); Henri Lichenstein, Guilford, CT (US)

(73) Assignee: AI Therapeutics, Inc., Guilford, CT (US)

( * ) Notice: Subject to any disclaimer, the term of this patent is extended or adjusted under 35 U.S.C. 154(b) by 0 days.

(21) Appl. No.: 15/524,841

(22) PCT Filed: Nov. 6, 2015

(86) PCT No.: PCT/US2015/059502
§ 371 (c)(1),
(2) Date: May 5, 2017

(87) PCT Pub. No.: WO2016/073871
PCT Pub. Date: May 12, 2016

(65) Prior Publication Data
US 2017/0333439 A1 Nov. 23, 2017

Related U.S. Application Data

(60) Provisional application No. 62/119,540, filed on Feb. 23, 2015, provisional application No. 62/115,228, filed on Feb. 12, 2015, provisional application No. 62/077,127, filed on Nov. 7, 2014.

(51) Int. Cl.
| *A61K 31/5377* | (2006.01) |
| *G01N 33/574* | (2006.01) |
| *A61K 45/06* | (2006.01) |
| *A61K 31/437* | (2006.01) |
| *A61K 31/44* | (2006.01) |
| *A61K 9/00* | (2006.01) |
| *A61P 35/04* | (2006.01) |

(52) U.S. Cl.
CPC ........ *A61K 31/5377* (2013.01); *A61K 9/0019* (2013.01); *A61K 9/0053* (2013.01); *A61K 31/437* (2013.01); *A61K 31/44* (2013.01); *A61K 45/06* (2013.01); *A61P 35/04* (2018.01); *G01N 33/5743* (2013.01); *G01N 33/57419* (2013.01); *G01N 2800/52* (2013.01)

(58) Field of Classification Search
CPC .. A61K 31/437; A61K 31/5377; A61K 45/06; A61K 9/0019; A61K 31/519; A61K 31/404; A61K 2300/00; A61K 31/44; A61K 9/0053; A61K 31/506; G01N 33/5743; G01N 2800/52; G01N 33/57419; A61P 35/00; A61P 35/04
USPC ..................... 514/1.1, 227.8, 256
See application file for complete search history.

(56) References Cited

U.S. PATENT DOCUMENTS

| 6,660,733 | B2 * | 12/2003 | Sun ...................... A61K 31/506 |
| | | | 514/227.8 |
| 6,693,097 | B2 * | 2/2004 | Ono ...................... A61K 31/506 |
| | | | 514/227.8 |
| 7,745,436 | B2 * | 6/2010 | Kostik ................. C07D 239/48 |
| | | | 514/235.8 |
| 7,863,270 | B2 | 1/2011 | Demko et al. |
| 7,923,557 | B2 | 4/2011 | Zhang et al. |
| 9,295,731 | B2 * | 3/2016 | Nguyen ................ A61K 45/06 |
| 10,179,135 | B2 * | 1/2019 | Lichenstein ........... A61K 45/06 |
| 10,206,910 | B2 * | 2/2019 | Beeharry ............... A61K 45/06 |
| 10,350,213 | B2 * | 7/2019 | Lichenstein ........ A61K 31/5377 |
| 2007/0112005 | A1 | 5/2007 | Chen et al. |
| 2011/0081338 | A1 | 4/2011 | Roberts et al. |
| 2011/0277018 | A1 | 11/2011 | Bosch |
| 2013/0267521 | A1 | 10/2013 | Castro et al. |
| 2017/0007613 | A1 * | 1/2017 | Lichenstein ........... A61K 45/06 |
| 2017/0020884 | A1 * | 1/2017 | Lichenstein ......... A61K 31/454 |
| 2017/0333408 | A1 * | 11/2017 | Beeharry ............... A61K 31/44 |
| 2018/0015098 | A1 * | 1/2018 | Lichenstein ....... A61K 31/5377 |
| 2018/0078561 | A1 * | 3/2018 | Beckett ............. A61K 31/5377 |

FOREIGN PATENT DOCUMENTS

| WO | 2005076843 A2 | 8/2005 |
| WO | 2005076843 A3 | 8/2005 |
| WO | 2006128129 A2 | 11/2006 |
| WO | 2006128129 A3 | 11/2006 |
| WO | WO-2006-128129 A2 | 11/2006 |
| WO | 2008008433 A2 | 1/2008 |

(Continued)

OTHER PUBLICATIONS

Wada et al., "Selective abrogation of Th1 response by STA-5326, a potent IL-12/IL-23 inhibitor", 2007 (originally published online Oct. 19, 2006), Blood, 109(3), pp. 1156-1164. (Year: 2007).*

(Continued)

*Primary Examiner* — My-Chau T. Tran
(74) *Attorney, Agent, or Firm* — Muriel Liberto, Esq.; Mintz Levin Cohn Ferris Glovsky and Popeo, P.C.

(57) ABSTRACT

The present invention relates to methods for treating melanoma with apilimod and related compositions and methods.

11 Claims, 4 Drawing Sheets

(56) References Cited

FOREIGN PATENT DOCUMENTS

| WO | 2008008433 A3 | 1/2008 |
|---|---|---|
| WO | WO-2013/152342 A1 | 10/2013 |
| WO | 2015112888 A1 | 7/2015 |
| WO | WO-2015-112888 A1 | 7/2015 |

OTHER PUBLICATIONS

Santosh K. Katiyar, "Interleukin-12 and photocarcinogenesis", 2007 (Available online Nov. 18, 2006), Toxicology and Applied Pharmacology, 224(3), pp. 220-227. (Year: 2007).*
Krausz et al., "A Phase IIa, Randomized, Double-Blind, Placebo-Controlled Trial of Apilimod Mesylate, an Interleukin-12/Interleukin-23 Inhibitor, in Patients With Rheumatoid Arthritis", 2012, Arthritis & Rheumatism, 64(6), pp. 1750-1755. (Year: 2012).*
Gayle et al., "Identification of apilimod as a first-in-class PIKfyve kinase inhibitor for treatment of B-cell non-Hodgkin lymphoma", Mar. 2017 (Prepublished online as Blood First Edition paper, Jan. 19, 2017), 129(3), pp. 1768-1778. (Year: 2017).*
Definition of stage III melanoma—NCI Dictionary of Cancer Terms—National Cancer Institute (https://www.cancer.gov/publications/dictionaries/cancer-terms/def/stage-iii-melanoma) (Year: 2018).*
Definition of stage IV melanoma—NCI Dictionary of Cancer Terms—National Cancer Institute (https://www.cancer.gov/publications/dictionaries/cancer-terms/def/stage-iv-melanoma) (Year: 2018).*
Jordan et al., "Vemurafenib for the treatment of melanoma", 2012, Expert Opin. Pharmacother., 13(17), pp. 2533-2543. (doi: 10.1517/14656566.2012.737780). (Year: 2012).*
Johansson et al., "BRAF inhibitors in cancer therapy", 2014, Pharmacology & Therapeutics, 142(2), pp. 176-182. (Available online Dec. 2013) (Year: 2014).*
Baird, A.M. et al., "IL-23R is Epigenetically Regulated and Modulated by Chemotherapy in Non-Small Cell Lung Cancer", *Frontiers in Oncology*, Jun. 19, 2013, pp. 1-9, vol. 3, Article 162.
International Search Report dated Dec. 23, 2015 for International Application No. PCT/US2015/059502, filed Nov. 6, 2015, 4 pages.
Langowski, J.L. et al., "IL-23 Promotes Tumour Incidence and Growth", *Nature*, Jul. 27, 2006, pp. 461-465, vol. 442, Nature Publishing Group, U.K.
Wada, Y. et al., "Selective Abrogation of Th1 Response by STA-5326, a Potent IL-12/IL-23 Inhibitor", *Blood*, Feb. 1, 2007, pp. 1156-1164, vol. 109, No. 3.
Chou, T.C. et al. (1984). "Quantitative analysis of dose-effect relationships: the combined effects of multiple drugs or enzyme inhibitors," *Adv Enzyme Regul* 22:27-55.
Liu, Q. et al. (2009). "mTOR Mediated Anti-Cancer Drug Discovery," *Drug Discov Today Ther* Strateg 6(2):47-55.
Puls, L.N. et al. (2011, e-published Apr. 26, 2011). "Current status of SRC inhibitors in solid tumor malignancies," *Oncologist* 16(5):566-578.
Aapro, MS. et al., (2006). "A Phase III, double-blind, randomized rial of palonosetron compared with ondansetron in preventing chemotherapy-induced nausea and vomiting following highly emetogenic chemotherapy." Annals of Oncology 17(9):1441-1449, col. 2; p. 1442, col. 1.
Cai X, et al. (Jul. 25, 2013). "PIKfyve, a class III PI kinase, is a target of the small molecular IL-12/IL-23 inhibitor apilimod and a player in the toll-like receptor signalling." Chemistry and Biology 20(7):912-921.
Extended European Search Report dated Sep. 4, 2017, for EP Application No. EP15740043.3, filed Jan. 23, 2015. 8 pages.
International Search Report issued in PCT/US2015/012733 dated Apr. 15, 2015.
Novero A, et al., (2014). "Ibrutinib for B-cell malignancies." Experimental Hematology & Oncology. 3:4.

* cited by examiner

APILIMOD FOR USE IN THE TREATMENT OF MELANOMA

RELATED APPLICATIONS

This application is a national stage entry, filed under 35 U.S.C. § 371, of International Application No. PCT/US2015/059502, filed on Nov. 6, 2015, which claims priority to U.S. Pat. App. Ser. No. 62/077,127, filed on Nov. 7, 2014, U.S. Pat. App. Ser. No. 62/115,228, filed on Feb. 12, 2015, and U.S. Pat. App. Ser. No. 62/119,540, filed on Feb. 23, 2015, the contents of which are hereby fully incorporated by reference.

FIELD OF THE INVENTION

The present invention relates to compositions comprising apilimod and methods of using same in the treatment of melanoma.

BACKGROUND OF THE INVENTION

Melanoma is a serious form of skin cancer that develops in the cells (melanocytes) that make our skin color. Melanoma is the sixth most common cancer in the United States, and the number of melanoma cases diagnosed annually is increasing faster than for any other cancer. An estimated 73,870 new cases of invasive melanoma will be diagnosed in the US in 2015. An estimated 9,940 people will die of melanoma in 2015. Melanoma accounts for less than two percent of skin cancer cases, but the vast majority of skin cancer deaths. 1 in 50 men and women will be diagnosed with melanoma of the skin during their lifetime.

Early-stage melanoma can often be completely removed via surgery of the affected area. But once it has metastasized, it is much harder to treat. In most cases, it is not possible to completely eliminate or cure the cancer once it has metastasized. Depending upon where and how big the metastases are, treatment may involve chemotherapy, surgery, gene therapy, immunotherapy, radiation therapy, and combinations of these. There remains a need for more effective and less toxic treatment options for melanoma.

SUMMARY OF THE INVENTION

The present invention is based in part on the surprising discovery that apilimod is a highly cytotoxic agent in melanoma cells, especially melanoma cells that are resistant to other therapies, and further in combination with certain chemotherapy agents.

In one aspect, the present disclosure provides a composition for treating melanoma in a subject in need thereof, the composition comprising a therapeutically effective amount of apilimod, or a pharmaceutically acceptable salt, solvate, clathrate, hydrate, polymorph, prodrug, analog or derivative thereof. In one embodiment, the apilimod is apilimod dimesylate. In embodiments, the composition is an oral dosage form or a dosage form suitable for intravenous administration. In embodiments, the melanoma is a stage III or IV melanoma, a melanoma that is refractory, or a melanoma that is malignant or metastatic.

In embodiments, the composition further comprises at least one additional active agent. In embodiments, the at least one additional active agent is a therapeutic agent or a non-therapeutic agent, or a combination thereof. In embodiments, the at least one additional active agent is a therapeutic agent. In embodiments, the therapeutic agent is selected from a protein kinase inhibitor, a platinum based anti-neoplastic agent, a topoisomerase inhibitor, a nucleoside metabolic inhibitor, an alkylating agent, an intercalating agent, a tubulin binding agent, PD-1/PDL-1 pathway inhibitor, and combinations thereof. In embodiments, the therapeutic agent is selected from the group consisting of vemurafenib, dacarbazine, temozolomide, Nab-paclitaxel, carmustine, cisplatin, carboplatin, vinblastine, ipilimumab, pembrolizumab (Keytruda™)), Interleukin-2 (IL-2, Proleukin™), pembrolizumab (Keytruda™), dabrafenib (Tafinlar™), vemurafenib (Zelboraf™), trametinib (Mekinist™), dasatinib (Sprycel™), imatinib (Gleevec™), and nilotinib (Tasigna™) and combinations thereof. In embodiments, the therapeutic agent is vemurafenib. In embodiments, the therapeutic agent is a PD-1/PDL-1 pathway inhibitor. In embodiments, the PD-1/PDL-1 pathway inhibitor is selected from pembrolizumab (Keytruda), avelumab, atezolizumab (MPDL3280A), nivolumab (BMS-936558), pidilizumab (MK-3475), MSB0010718C, and MEDI4736.

In embodiments, the composition further comprises a non-therapeutic agent selected to ameliorate one or more side effects of the apilimod. In embodiments, the non-therapeutic agent is selected from the group consisting of ondansetron, granisetron, dolasetron and palonosetron. In embodiments, the non-therapeutic agent is selected from the group consisting of pindolol and risperidone.

In one aspect, the present disclosure provides a method for treating melanoma in a subject in need thereof, the method comprising administering to the subject a therapeutically effective amount of a composition comprising apilimod, wherein the apilimod is apilimod itself (i.e., apilimod free base) or a pharmaceutically acceptable salt, solvate, clathrate, hydrate, polymorph, prodrug, analog or derivative thereof. In one embodiment, the apilimod is apilimod dimesylate.

In embodiments, the method further comprises administering at least one additional active agent to the subject. The at least one additional active agent may be a therapeutic agent or a non-therapeutic agent, or a combination thereof. The at least one additional active agent may be administered in a single dosage form with the apilimod, or in a separate dosage form.

In embodiments, the at least one additional active agent is a tyrosine kinase inhibitor. In embodiments, the tyrosine kinase inhibitor is a B-Raf enzyme inhibitor. In embodiments, the at least one additional active agent is vemurafenib. In one embodiment, the method comprises administering apilimod and vemurafenib together in a combination therapy regimen for the treatment of melanoma. In one embodiment, the melanoma is a late-stage melanoma. In one embodiment, the late-stage melanoma is resistant to vemurafenib alone.

In embodiments, the at least one additional active agent is a therapeutic agent selected from the group consisting of a protein kinase inhibitor, a platinum based anti-neoplastic agent, a topoisomerase inhibitor, a nucleoside metabolic inhibitor, an alkylating agent, an intercalating agent, a tubulin binding agent, a BRAF inhibitor, and combinations thereof. In embodiments, the therapeutic agent is a protein kinase inhibitor, an alkylating agent, an intercalating agent, a tubulin binding agent, and combinations thereof. In embodiments, the therapeutic agent selected from the group consisting of vemurafenib, ibrutinib, rituximab, doxorubicin, vincristine, velcade, and everolimus, and combinations thereof. In embodiments, the at least one additional active agent is a therapeutic agent selected from vemurafenib, dacarbazine, temozolomide, Nab-paclitaxel, carmustine, cisplatin, carboplatin, vinblastine, ipilimumab, pembrolizumab (Keytruda™)), Interleukin-2 (IL-2, Proleukin™), pembrolizumab (Keytruda™), dabrafenib (Tafinlar™), vemurafenib (Zelboraf™), trametinib (Mekinist™), dasatinib (Sprycel™), imatinib (Gleevec™), and nilotinib (Tasigna™) and combinations thereof. In embodiments, the at least one additional active agent is a Bcl-2 inhibitor. In one embodiment, the Bcl-2 inhibitor is ABT-199 or navitoclax.

In embodiments, the at least one additional active agent is a non-therapeutic agent selected to ameliorate one or more side effects of the apilimod. In one embodiment, the non-therapeutic agent is selected from the group consisting of ondansetron, granisetron, dolasetron and palonosetron. In embodiments, the non-therapeutic agent is selected from the group consisting of pindolol and risperidone.

In embodiments, the composition is an oral dosage form. In other embodiments, the composition is a dosage form suitable for intravenous administration. In one embodiment, where the dosage form is suitable for intravenous administration, administration is by a single injection or by a drip bag. In other embodiments, the composition is a dosage form suitable for topical administration by a cream, lotion or gel.

In embodiments of the methods described here, the subject is a human melanoma patient. In embodiments, the human melanoma patient in need of treatment is one having late-stage, malignant or metastatic melanoma. In embodiments, the human melanoma patient in need of treatment is one whose cancer is refractory to a standard chemotherapy regimen. In embodiments, the human melanoma patient in need of treatment is one whose melanoma has recurred following treatment with a standard chemotherapy regimen.

In embodiments, the melanoma is selected from superficial spreading melanoma, lentigo maligna, acral lentiginous melanoma, and nodular melanoma. In one embodiment, the standard chemotherapy regimen comprises one or more therapeutic agents selected from the group consisting of dacarbazine, temozolomide, Nab-paclitaxel, carmustine, cisplatin, carboplatin, and vinblastine. In one embodiment, the immunotherapy regimen comprises one or more therapeutic agents selected from the group consisting of anti-CTLA4 antibodies (e.g., ipilimumab); PD-1/PDL-1 pathway inhibitors, e.g., pembrolizumab (Keytruda), avelumab, atezolizumab (MPDL3280A), nivolumab (BMS-936558), pidilizumab (MK-3475), MSB0010718C, and MEDI4736; AMP-224, and Interleukin-2 (IL-2, aldesleukin, Proleukin) In one embodiment, the targeted therapy regimen comprises one or more therapeutic agents selected from the group consisting of BRAF inhibitors (e.g., dabrafenib (Tafinlar) and vemurafenib (Zelboraf), MEK inhibitors (e.g., trametinib (Mekinist)) and KIT inhibitors (e.g., dasatinib (Sprycel), imatinib (Gleevec), and nilotinib (Tasigna)).

In embodiments, the method is a method of treating a melanoma using a combination therapy comprising apilimod and a chemotherapy regimen for the treatment of the melanoma. In one embodiment, the apilimod is administered as an adjunctive therapy to the chemotherapy regimen. In embodiments, the chemotherapy regimen comprises one or more of PD-1/PDL-1 pathway inhibitors selected from pembrolizumab (Keytruda), avelumab, atezolizumab (MPDL3280A), nivolumab (BMS-936558), pidilizumab (MK-3475), MSB0010718C, and MEDI4736. In embodiments, the chemotherapy regimen comprises one or more of dacarbazine, temozolomide, Nab-paclitaxel, carmustine, cisplatin, carboplatin, and vinblastine for the treatment of malignant or metastatic melanoma. In embodiments, the chemotherapy regimen comprises one or more of vemurafenib, dabrafenib and trametinib for metastatic melanoma. In one embodiment, the chemotherapy regimen comprises one or more of high dose interleukin-2 and ipilimumab.

In embodiments, the disclosure provides methods for inducing or potentiating autophagy or apoptosis in a melanoma cell. In accordance with this embodiment, the melanoma cell may be in vitro or in vivo. In one embodiment, the melanoma cell is in vitro and is derived from Yulac614, RPM19951, MEL-JUSO, SK-MEL-2, SK-MEL-31, A101D, and A2058 cells. In one embodiment, the melanoma cell is in vivo in a mammalian subject at a site other than the skin. In one embodiment, the melanoma cell is a late stage melanoma. In one embodiment, the melanoma cell is a metastatic cell or a cell that has metastasized.

The disclosure also provides a method for identifying a human melanoma patient for treatment with a combination therapy comprising apilimod and vemurafenib, the method comprising assaying a biological sample of the subject's cancer for one or more of the V600E BRAF protein mutation, the V600K BRAF protein mutation, or the genetic equivalents thereof, wherein a subject having either of these mutations is identified as a patient for treatment with a combination therapy comprising apilimod and vemurafenib.

DETAILED DESCRIPTION OF THE INVENTION

The present disclosure provides compositions and methods related to the use of apilimod for treating melanoma in a subject, preferably a human subject, in need of such treatment. The disclosure generally relates to new uses of apilimod based upon the surprising discovery of apilimod's cytotoxic activity against a range of cancer cells such as melanoma. In addition, the present invention provides novel therapeutic approaches to melanoma treatment based upon combination therapy utilizing apilimod and at least one additional therapeutic agent. The combination therapies described herein exploit the unique cytotoxic activity of apilimod which can provide a synergistic effect when combined with other therapeutic agents, including for example, anti-cancer agents.

As used herein, the term "apilimod" may refer to apilimod itself (i.e., apilimod free base), or may encompass pharmaceutically acceptable salts, solvates, clathrates, hydrates, polymorphs, prodrugs, analogs or derivatives of apilimod, as described below. In embodiments, the apilimod is apilimod dimesylate. The structure of apilimod is shown in Formula I:

(I)

The IUPAC name of apilimod is: (E)-4-(6-(2-(3-methyl-benzylidene)hydrazinyl)-2-(2-(pyridin-2-yl)ethoxy)pyrimidin-4-yl)morpholine) and the CAS number is 541550-19-0.

Apilimod can be prepared, for example, according to the methods described in U.S. Pat. Nos. 7,923,557, and 7,863,270, and WO 2006/128129.

As used herein, the term "pharmaceutically acceptable salt," is a salt formed from, for example, an acid and a basic group of an apilimod composition. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts. In a preferred embodiment, the salt of apilimod comprises methanesulfonate.

The term "pharmaceutically acceptable salt" also refers to a salt prepared from an apilimod composition having an acidic functional group, such as a carboxylic acid functional group, and a pharmaceutically acceptable inorganic or organic base.

The term "pharmaceutically acceptable salt" also refers to a salt prepared from an apilimod composition having a basic functional group, such as an amino functional group, and a pharmaceutically acceptable inorganic or organic acid.

The salts of the compounds described herein can be synthesized from the parent compound by conventional chemical methods such as methods described in Pharmaceutical Salts: Properties, Selection, and Use, P. Hemrich Stahl (Editor), Camille G. Wermuth (Editor), ISBN: 3-90639-026-8, August 2002. Generally, such salts can be prepared by reacting the parent compound with the appropriate acid in water or in an organic solvent, or in a mixture of the two.

One salt form of a compound described herein can be converted to the free base and optionally to another salt form by methods well known to the skilled person. For example, the free base can be formed by passing the salt solution through a column containing an amine stationary phase (e.g. a Strata-NH$_2$ column). Alternatively, a solution of the salt in water can be treated with sodium bicarbonate to decompose the salt and precipitate out the free base. The free base may then be combined with another acid using routine methods.

As used herein, the term "polymorph" means solid crystalline forms of a compound of the present invention (e.g., apilimod) or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention (e.g., apilimod) or a salt thereof, which further includes a stoichiometric or non-stoichiometric amount of water bound by non-covalent intermolecular forces.

As used herein, the term "clathrate" means a compound of the present invention (e.g., apilimod) or a salt thereof in the form of a crystal lattice that contains spaces (e.g., channels) that have a guest molecule (e.g., a solvent or water) trapped within.

As used herein, the term "prodrug" means a derivative of a compound described herein (e.g., apilimod) that can hydrolyze, oxidize, or otherwise react under biological conditions (in vitro or in vivo) to provide a compound of the invention. Prodrugs may only become active upon such reaction under biological conditions, or they may have activity in their unreacted forms. Examples of prodrugs contemplated in this invention include, but are not limited to, analogs or derivatives of a compound described herein (e.g., apilimod) that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed).

As used herein, the term "solvate" or "pharmaceutically acceptable solvate," is a solvate formed from the association of one or more solvent molecules to one of the compounds disclosed herein (e.g., apilimod). The term solvate includes hydrates (e.g., hemi-hydrate, mono-hydrate, dihydrate, tri-hydrate, tetrahydrate, and the like).

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

Melanoma

Melanoma is a type of skin cancer which forms from melanocytes (pigment-containing cells in the skin), which are found in the epidermis of the skin. The epidermis is the upper or outer layer of the two main layers of cells that make up the skin and is separated from the deeper layers of the skin by the basement membrane. When a skin cancer such as melanoma becomes more advanced, it generally penetrated the epidermis and grows through the membrane into the deeper layers of the skin to gain access to the blood supply, which enables the tumor to metastasize.

There are four basic types of melanoma. Three of them begin in situ meaning they occupy only the top layers of the skin, and sometimes become invasive; the fourth is invasive from the start. Invasive melanomas are more serious, as they have penetrated deeper into the skin and may have spread to other areas of the body.

Superficial spreading melanoma is by far the most common type, accounting for about 70 percent of all cases. This is the one most often seen in young people. As the name suggests, this melanoma grows along the top layer of the skin for a fairly long time before penetrating more deeply.

Lentigo maligna is similar to the superficial spreading type, as it also remains close to the skin surface for quite a while, and usually appears as a flat or mildly elevated mottled tan, brown or dark brown discoloration. This type of in situ melanoma is found most often in the elderly, arising on chronically sun-exposed, damaged skin on the face, ears, arms and upper trunk. When this cancer becomes invasive, it is referred to as lentigo maligna melanoma.

Acral lentiginous melanoma also spreads superficially before penetrating more deeply. It is quite different from the others, though, as it usually appears as a black or brown discoloration under the nails or on the soles of the feet or palms of the hands. This type of melanoma is sometimes found on dark-skinned people, and can often advance more quickly than superficial spreading melanoma and lentigo maligna. It is the most common melanoma in African-Americans and Asians, and the least common among Caucasians.

Nodular melanoma is usually invasive at the time it is first diagnosed. The malignancy is recognized when it becomes a bump. It is usually black, but occasionally is blue, gray, white, brown, tan, red or skin tone.

Methods of Treatment

The disclosure provides methods for the treatment of melanoma in a subject in need thereof by administering to the subject a therapeutically effective amount of apilimod, or a pharmaceutically acceptable salt, solvate, clathrate, hydrate, polymorph, prodrug, analog or derivative thereof. In embodiments, the apilimod is apilimod dimesylate. The disclosure further provides for the use of apilimod in the preparation of a medicament for the treatment of melanoma.

In the context of the methods described herein, the amount of apilimod administered to the subject is a therapeutically effective amount. The term "therapeutically effective amount" refers to an amount sufficient to treat, ameliorate a symptom of, reduce the severity of, or stabilize or cause the regression of melanoma in the subject being treated, or to enhance or improve the therapeutic effect of another therapy, such as vemurafenib.

In accordance with the methods described herein, a "subject in need of" is a subject having melanoma. In one aspect, the subject is a human patient having malignant melanoma or late-stage melanoma. In this context, "stage" refers to the clinical stage of the cancer. For example, stage 0 to 2 melanoma or stage 3 or stage 4 melanoma. In one embodiment, the subject is a human patient having stage 3 or stage 4 melanoma. The subject in need thereof can be one that is "non-responsive" or "refractory" to a currently available therapy, for example the subject's cancer may be resistant or refractor to treatment with vemurafenib. In this context, the terms "non-responsive" and "refractory" refer to the subject's response to therapy as not clinically significant according to the definition for a clinical response in standard medical practice.

Combination Therapy

The disclosure also provides methods comprising combination therapy with apilimod. As used herein, "combination therapy" or "co-therapy" includes the administration of a therapeutically effective amount of a primary therapy (e.g., apilimod) with at least one additional therapeutic agent, as part of a specific treatment regimen intended to provide a beneficial effect from the co-action of the primary therapy and the additional therapeutic agent. "Combination therapy" is not intended to encompass the administration of two or more therapeutic compounds as part of separate monotherapy regimens that incidentally and arbitrarily result in a beneficial effect that was not intended or predicted.

In one embodiment, the method is a method of treating melanoma using a combination therapy comprising apilimod and a chemotherapy regimen for the treatment of melanoma. In one embodiment, the chemotherapy regimen is selected from dacarbazine, temozolomide, Nab-paclitaxel, carmustine, cisplatin, carboplatin, vinblastine, and combinations thereof.

In embodiments, the at least one additional active agent may be a therapeutic agent, for example an anti-cancer agent or a cancer chemotherapeutic agent, or a non-therapeutic agent, and combinations thereof. With respect to therapeutic agents, the beneficial effect of the combination includes, but is not limited to, pharmacokinetic or pharmacodynamic co-action resulting from the combination of therapeutically active compounds. With respect to non-therapeutic agents, the beneficial effect of the combination may relate to the mitigation of a toxicity, side effect, or adverse event associated with a therapeutically active agent in the combination.

In embodiments, the at least one additional agent is a non-therapeutic agent which mitigates one or more side effects of the apilimod, the one or more side effects selected from any of nausea, vomiting, headache, dizziness, light-headedness, drowsiness and stress. In one aspect of this embodiment, the non-therapeutic agent is an antagonist of a serotonin receptor, also known as 5-hydroxytryptamine receptors or 5-HT receptors. In one aspect, the non-therapeutic agent is an antagonist of a $5-HT_3$ or $5-HT_{1a}$ receptor. In one aspect, the non-therapeutic agent is selected from the group consisting of ondansetron, granisetron, dolasetron and palonosetron. In another aspect, the non-therapeutic agent is selected from the group consisting of pindolol and risperidone.

In embodiments, the at least one additional agent is a therapeutic agent. In one embodiment, the therapeutic agent is an anti-cancer agent. In embodiments, the anti-cancer agent is vemurafenib. In one embodiment, the apilimod is administered along with vemurafenib in a single dosage form or in separate dosage forms. In one embodiment, the dosage form is an oral dosage form. In another embodiment, the dosage form is suitable for intravenous administration.

In embodiments, the anti-cancer agent is a drug that is approved for use in treating melanoma. Non-limiting examples of such drugs include aldesleukin, dabrafenib, dacarbazine, DTIC-Dome (darcarbazine), intronA (recombinant interferon Alsfa-2b), ipilimumab, keytruda (pembrolizumab), mekinist (trametinib), nivolumab, peginterferon alfa-2b, PEG-Intron (peginterferon alfa-2b), pembrolizumab, proleukin (aldesleukin), recombinant interferon alfa-2b, sylatron (pegonterferon alfa-2b), tafinlar (dabrafenib), trametinib, vemurafenib, yervoy (ipilimumab), zelboraf (vermurafenib)

In embodiments, the anti-cancer agent is selected from an inhibitor of EZH2, e.g., EPZ-6438. In one embodiment, the anti-cancer agent is selected from taxol, vincristine, doxorubicin, temsirolimus, carboplatin, ofatumumab, rituximab, and combinations thereof.

In embodiments, the anti-cancer agent is a Bcl-2 inhibitor. In one embodiment, the Bcl-2 inhibitor is ABT-199 or navitoclax.

In embodiments, the at least one additional agent is selected from chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, or a combination thereof.

In embodiments, the at least one additional agent is a monoclonal antibody such as, for example, alemtuzumab, bevacizumab, catumaxomab, cetuximab, edrecolomab, gemtuzumab, ofatumumab, panitumumab, rituximab, trastuzumab, eculizumab, efalizumab, muromab-CD3, natalizumab, adalimumab, afelimomab, certolizumab pegol, golimumab, infliximab, basiliximab, canakinumab, daclizumab, mepolizumab, tocilizumab, ustekinumab, ibritumomab tiuxetan, tositumomab, abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, and zalutumumab.

In embodiments, the at least one additional inhibitor is a BRAF inhibitor, a MEK inhibitor, a PD-1/PD-L1 inhibitor or a check point inhibitor.

In embodiments, the PD-1/PDL-1 pathway inhibitor is selected from pembrolizumab (Keytruda), avelumab, atezolizumab (MPDL3280A), nivolumab (BMS-936558), pidilizumab (MK-3475), MSB0010718C, and MEDI4736.

In the context of combination therapy, administration of the apilimod may be simultaneous with or sequential to the administration of the one or more additional active agents. In embodiments, administration of the different components of a combination therapy may be at different frequencies. The one or more additional agents may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a compound of the present invention.

The one or more additional active agents can be formulated for co-administration with the apilimod in a single dosage form, as described in greater detail herein. The one or more additional active agents can be administered separately from the dosage form that comprises the apilimod. When the additional active agent is administered separately from the apilimod, it can be by the same or a different route of administration as the apilimod.

Preferably, the administration of apilimod in combination with one or more additional agents provides a synergistic response in the subject being treated. In this context, the term "synergistic" refers to the efficacy of the combination being more effective than the additive effects of either single therapy alone. The synergistic effect of a combination therapy can permit the use of lower dosages and/or less frequent administration of at least one agent in the combination compared to its dose and/or frequency outside of the combination. Additional beneficial effects of the combination can be manifested in the avoidance or reduction of adverse or unwanted side effects associated with the use of either therapy in the combination alone (also referred to as monotherapy).

"Combination therapy" also embraces the administration of a therapeutic compound in combination with one or more non-drug therapies (e.g., surgery or radiation treatment). Where the combination therapy further comprises a non-drug treatment, the non-drug treatment may be conducted at any suitable time so long as a beneficial effect from the co-action of the combination of the therapeutic compounds and non-drug treatment is achieved. For example, in appropriate cases, the beneficial effect is still achieved when the non-drug treatment is temporally removed from the administration of the therapeutic compounds, perhaps by days or even weeks.

In accordance with any of the methods described herein, a therapeutically effective amount of apilimod can range from about 0.001 mg/kg to about 1000 mg/kg, about 0.01 mg/kg to about 100 mg/kg, about 10 mg/kg to about 250 mg/kg, about 0.1 mg/kg to about 15 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents. See, e.g., U.S. Pat. No. 7,863,270, incorporated herein by reference.

In embodiments, apilimod is administered at a dosage regimen of 30-1000 mg/day (e.g., 30, 35, 40, 45, 50, 55, 60, 65, 70, 75, 80, 85, 90, 95, 100, 125, 150, 175, 200, 225, 250, 275, or 300 mg/day) for at least 1 week (e.g., 1, 2, 3, 4, 5, 6, 7, 8, 9, 10, 11, 12, 36, 48, or more weeks). Preferably, the apilimod is administered at a dosage regimen of 100-1000 mg/day for 4 or 16 weeks. Alternatively or subsequently, the apilimod is administered at a dosage regimen of 100 mg-300 mg twice a day for 8 weeks, or optionally, for 52 weeks. Alternatively or subsequently, the apilimod is administered at a dosage regimen of 50 mg-1000 mg twice a day for 8 weeks, or optionally, for 52 weeks.

A therapeutically effective amount of the apilimod can be administered once daily, from two to five times daily, up to two times or up to three times daily, or up to eight times daily. In embodiments, the apilimod is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

A "subject" as used in the context of the methods described herein is preferably a human subject but may also include other mammals. The mammal can be e.g., any mammal, e.g., a human, primate, vertebrate, bird, mouse, rat, fowl, dog, cat, cow, horse, goat, camel, sheep or a pig. The term "patient" refers to a human subject.

The disclosure also provides a monotherapy for the treatment of melanoma using apilimod. As used herein, "monotherapy" refers to the administration of a single active or therapeutic compound, i.e., apilimod, to a subject in need thereof.

As used herein, "treatment", "treating" or "treat" describes the management and care of a patient for the purpose of combating a disease, condition, or disorder and includes the administration of an apilimod composition to alleviate the symptoms or complications of a disease, condition or disorder, or to eliminate the disease, condition or disorder.

In embodiments, the administration of apilimod leads to the elimination of a symptom or complication of the melanoma being treated, however, elimination is not required. In one embodiment, the severity of the symptom is decreased. In the context of cancer, such symptoms may include clinical markers of severity or progression including the degree to which a tumor secrets growth factors, degrades the extracellular matrix, becomes vascularized, loses adhesion to juxtaposed tissues, or metastasizes, as well as the number of metastases.

Treating melanoma according to the methods described herein can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating melanoma according to the methods described herein can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating melanoma according to the methods described herein can result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating melanoma according to the methods described herein can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating melanoma according to the methods described herein can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating melanoma according to the methods described herein can result in increase in average survival time of a population of treated subjects in comparison to a population receiving monotherapy with a drug that is not apilimod. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating melanoma according to the methods described herein can result in a decrease in the mortality rate of a population of treated subjects in comparison to a population receiving carrier alone. Treating melanoma according to the methods described herein can result in a decrease in the mortality rate of a population of treated subjects in comparison to an untreated population. Treating melanoma according to the methods described herein can result in a decrease in the mortality rate of a population of treated subjects in comparison to a population receiving monotherapy with a drug that is not apilimod. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating melanoma according to the methods described herein can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time. In one embodiment, after treatment the tumor growth rate may be about zero and is determined to maintain the same size, e.g., has stopped growing.

Treating a melanoma according to the methods described herein can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

As used herein, the term "selectively" means tending to occur at a higher frequency in one population than in another population. The compared populations can be cell populations. Preferably, apilimod acts selectively on hyper-proliferating cells or abnormally proliferating cells, compared to normal cells. As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms. Preferably, apilimod acts selectively to modulate one molecular target (e.g., a target kinase) but does not significantly modulate another molecular target (e.g., a non-target kinase). The disclosure also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in diseased or hyper-proliferating cells if it occurred greater than twice as frequently in diseased or hyper-proliferating cells as compared to normal cells.

Pharmaceutical Compositions and Formulations

The disclosure provides compositions comprising apilimod that are pharmaceutically acceptable compositions suitable for use in a mammal, preferably a human. In this context, the compositions may further comprise at least one pharmaceutically acceptable excipient or carrier, wherein the amount is effective for the treatment of melanoma. In embodiments, the apilimod is apilimod dimesylate.

In embodiments, the apilimod is combined with at least one additional active agent in a single dosage form. In one embodiment, the composition further comprises an antioxidant.

In embodiments, the at least one additional active agent is a therapeutic agent selected from the group consisting of a protein kinase inhibitor, a platinum based anti-neoplastic agent, a topoisomerase inhibitor, a nucleoside metabolic inhibitor, an alkylating agent, an intercalating agent, a tubulin binding agent, a BRAF inhibitor, and combinations thereof. In embodiments, the therapeutic agent is a protein kinase inhibitor, an alkylating agent, an intercalating agent, a tubulin binding agent, a corticosteroid, and combinations thereof. In embodiments, the therapeutic agent is selected from the group consisting of vemurafenib, ibrutinib, rituximab, doxorubicin, prednisolone, vincristine, velcade, and everolimus, and combinations thereof.

In embodiments, the at least one additional active agent is a BRAF inhibitor, a MEK inhibitor, a PD-1/PD-L1 inhibitor, or a check point inhibitor.

In embodiments, the PD-1/PDL-1 pathway inhibitor is selected from pembrolizumab (Keytruda), avelumab, atezolizumab (MPDL3280A), nivolumab (BMS-936558), pidilizumab (MK-3475), MSB0010718C, and MEDI4736.

In embodiments, the at least one additional active agent is a therapeutic agent selected from the group consisting of dacarbazine, temozolomide, Nab-paclitaxel, carmustine, cisplatin, carboplatin, vinblastine, ipilimumab, Interleukin-2 (IL-2, Proleukin), pembrolizumab (Keytruda), dabrafenib (Tafinlar), vemurafenib (Zelboraf), trametinib (Mekinist), dasatinib (Sprycel), imatinib (Gleevec), and nilotinib (Tasigna) and combinations thereof.

In embodiments, the at least one additional active agent is a non-therapeutic agent selected to ameliorate one or more side effects of the apilimod. In embodiments, the non-therapeutic agent is selected from the group consisting of ondansetron, granisetron, dolasetron and palonosetron. In embodiments, the non-therapeutic agent is selected from the group consisting of pindolol and risperidone.

In embodiments, the at least one additional active agent is selected from an inhibitor of BRAF, an inhibitor of the Raf/MEK/ERK pathway, an inhibitor of the mTOR pathway, a PI3K inhibitor, a dual PI3K/mTOR inhibitor, a SRC inhibitor, a VEGF inhibitor, a Janus kinase (JAK) inhibitor, a Raf inhibitor, an Erk inhibitor, a farnesyltransferase inhibitor, a histone deacetylase inhibitor, an anti-mitotic agent, a multi-drug resistance efflux inhibitor, an antibiotic, and a therapeutic antibody. In one embodiment, the at least one additional active agent is selected from a farnesyltransferase inhibitor (e.g., tipifarnib), an anti-mitotic agent (e.g., docetaxel), a histone deacetylase inhibitor (e.g., vorinostat), and a multi-drug resistance efflux inhibitor.

In embodiments, the mTOR inhibitor is selected from the group consisting of rapamycin (also referred to as sirolimus), everolimus, temsirolimus, ridaforolimus, umirolimus, zotarolimus, AZD8055, INK128, WYE-132, Torin-1, pyrazolopyrimidine analogs PP242, PP30, PP487, PP121, KU0063794, KU-BMCL-200908069-1, Wyeth-BMCL- 200910075-9b, INK-128, XL388, AZD8055, P2281, and P529. See, e.g., Liu et al. *Drug Disc. Today Ther. Strateg.,* 6(2): 47-55 (2009).

In embodiments, the mTOR inhibitor is trans-4-[4-amino-5-(7-methoxy-1H-indol-2-yl)imidazo[5,1-f][1,2,4]triazin-7-yl]cyclohexane carboxylic acid (also known as OSI-027), and any salts, solvates, hydrates, and other physical forms, crystalline or amorphous, thereof. See US 2007/0112005. OSI-027 can be prepared according to US 2007/0112005, incorporated herein by reference. In one embodiment, the mTOR inhibitor is OXA-01. See e.g., WO 2013152342 A1.

In embodiments, the PI3K inhibitor is selected from the group consisting of GS-1101 (Idelalisib), GDC0941 (Pictilisib), LY294002, BKM120 (Buparlisib), PI-103, TGX-221, IC-87114, XL 147, ZSTK474, BYL719, AS-605240, PIK-75, 3-methyladenine, A66, PIK-93, PIK-90, AZD6482, IPI-145 (Duvelisib), TG100-115, AS-252424, PIK294, AS-604850, GSK2636771, BAY 80-6946 (Copanlisib), CH5132799, CAY10505, PIK-293, TG100713, CZC24832 and HS-173.

In embodiments, the dual PI3K/mTOR inhibitor is selected from the group consisting of, GDC-094, WAY-001, WYE-354, WAY-600, WYE-687, Wyeth-BMCL-200910075-16b, Wyeth-BMCL-200910096-27, KU0063794 and KUBMCL-200908069-5, NVP-BEZ235, XL-765, PF-04691502, GDC-0980 (Apitolisib), GSK1059615, PF-05212384, BGT226, PKI-402, VS-558 and GSK2126458. See, e.g., Liu et al. Drug Disc. Today Ther. Strateg., 6(2): 47-55 (2009), incorporated herein by reference.

In embodiments, the mTOR pathway inhibitor is a polypeptide (e.g., an antibody or fragment thereof) or a nucleic acid (e.g., a double-stranded small interfering RNA, a short hairpin RNA, a micro-RNA, an antisense oligonucleotide, a locked nucleic acid, or an aptamer) that binds to and inhibits the expression level or activity or a protein (or nucleic acid encoding the protein) in the mTOR pathway. For example, the polypeptide or nucleic acid inhibits mTOR Complex 1 (mTORC1), regulatory-associated protein of mTOR (Raptor), mammalian lethal with SEC13 protein 8 (MLST8), proline-rich Akt substrate of 40 kDa (PRAS40), DEP domain-containing mTOR-interacting protein (DEPTOR), mTOR Complex 2 (mTORC2), rapamycin-insensitive companion of mTOR (RICTOR), G protein beta subunit-like (GβL), mammalian stress-activated protein kinase interacting protein 1 (mSIN1), paxillin, RhoA, Ras-related C3 botulinum toxin substrate 1 (Rac1), Cell division control protein 42 homolog (Cdc42), protein kinase C α (PKCα), the serine/threonine protein kinase Akt, phosphoinositide 3-kinase (PI3K), p70S6K, Ras, and/or eukaryotic translation initiation factor 4E (eIF4E)-binding proteins (4EBPs), or the nucleic acid encoding one of these proteins.

In embodiments, the SRC inhibitor is selected from the group consisting of bosutinib, saracatinib, dasatinib, ponatinib, KX2-391, XL-228, TG100435/TG100855, and DCC2036. See, e.g., Puls et al. *Oncologist.* 2011 May; 16(5): 566-578. In one embodiment, the SRC inhibitor is a polypeptide (e.g., an antibody or fragment thereof) or nucleic acid (e.g., a double-stranded small interfering RNA, a short hairpin RNA, a micro-RNA, an antisense oligonucleotide, a locked nucleic acid, or an aptamer) that binds to and inhibits the expression level or activity of the SRC protein or a nucleic acid encoding the SRC protein.

In embodiments, the VEGF inhibitor is selected from bevacizumab, sunitinib, pazopanib, axitinib, sorafenib, regorafenib, lenvatinib, and motesanib. In one embodiment, the VEGF inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a VEGF protein, a VEGF receptor protein, or a nucleic acid encoding one of these proteins. For example, the VEGF inhibitor is a soluble VEGF receptor (e.g., a soluble VEGF-C/D receptor (sVEGFR-3)).

In embodiments, the JAK inhibitor is selected from facitinib, ruxolitinib, baricitinib, CYT387 (CAS number 1056634-68-4), lestaurtinib, pacritinib, and TG101348 (CAS number 936091-26-8). In one embodiment, the JAK inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a JAK (e.g., JAK1, JAK2, JAK3, or TYK2) or a nucleic acid encoding the JAK protein.

In embodiments, the Raf inhibitor is selected from PLX4032 (vemurafenib), sorafenib, PLX-4720, GSK2118436 (dabrafenib), GDC-0879, RAF265, AZ 628, NVP-BHG712, SB90885, ZM 336372, GW5074, TAK-632, CEP-32496 and LGX818 (Encorafenib). In one embodiment, the Raf inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a Raf (e.g., A-Raf, B-Raf, C-Raf) or a nucleic acid encoding the Raf protein. In one embodiment, the MEK inhibitor is selected from AZD6244 (Selumetinib), PD0325901, GSK1120212 (Trametinib), U0126-EtOH, PD184352, RDEA119 (Rafametinib), PD98059, BIX 02189, MEK162 (Binimetinib), AS-703026 (Pimasertib), SL-327, BIX02188, AZD8330, TAK-733 and PD318088. In one embodiment, the MEK inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a MEK (e.g., MEK-1, MEK-2) or a nucleic acid encoding the MEK protein.

In embodiments, the Akt inhibitor is selected from MK-2206, KRX-0401 (perifosine), GSK690693, GDC-0068 (Ipatasertib), AZD5363, CCT128930, A-674563, PHT-427. In one embodiment, the Akt inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of a Akt (e.g., Akt-1, Akt-2, Akt-3) or a nucleic acid encoding the Akt protein.

In embodiments, the farnesyltransferase inhibitor is selected from LB42708 or tipifarnib. In one embodiment, the farnesyltransferase inhibitor is a polypeptide (e.g., an antibody or fragment thereof) or nucleic acid (e.g., a double-stranded small interfering RNA, a short hairpin RNA, a micro-RNA, an antisense oligonucleotide, a morpholino, a locked nucleic acid, or an aptamer) that binds to and inhibits the expression level or activity of farnesyltransferase or a nucleic acid encoding the farnesyltransferase protein. In one embodiment, the histone modulating inhibitor is selected from anacardic acid, C646, MG149 (histone acetyltransferase), GSK J4 Hcl (histone demethylase), GSK343 (active against EZH2), BIX 01294 (histone methyltransferase), MK0683 (Vorinostat), MS275 (Entinostat), LBH589 (Panobinostat), Trichostatin A, MGCD0103 (Mocetinostat), Tasquinimod, TMP269, Nexturastat A, RG2833, PDX101 (Belinostat).

In embodiments, the anti-mitotic agent is selected from Griseofulvin, vinorelbine tartrate, paclitaxel, docetaxel, vincristine, vinblastine, Epothilone A, Epothilone B, ABT-751, CYT997 (Lexibulin), vinflunine tartrate, Fosbretabulin, GSK461364, ON-01910 (Rigosertib), Ro3280, BI2536, NMS-P937, BI 6727 (Volasertib), HMN-214 and MLN0905.

In embodiments, the polyether antibiotic is selected from sodium monensin, nigericin, valinomycin, salinomycin.

A "pharmaceutical composition" is a formulation containing the compounds described herein in a pharmaceutically acceptable form suitable for administration to a subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

For example, the dosage unit form can comprise 1 nanogram to 2 milligrams, or 0.1 milligrams to 2 grams; or from 10 milligrams to 1 gram, or from 50 milligrams to 500 milligrams or from 1 microgram to 20 milligrams; or from 1 microgram to 10 milligrams; or from 0.1 milligrams to 2 milligrams.

The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present invention may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the invention are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The disclosure also provides packaging and kits comprising pharmaceutical compositions for use in the methods described here. The kit can comprise one or more containers selected from the group consisting of a bottle, a vial, an ampoule, a blister pack, and a syringe. The kit can further include one or more of instructions for use in treating and/or preventing a disease, condition or disorder of the present invention, one or more syringes, one or more applicators, or a sterile solution suitable for reconstituting a pharmaceutical composition of the present invention.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1: Synergistic Activity Between Apilimod and Vemurafenib

Yulac614 (resistant to vemurafenib, see Choi et al. 2014) cells were used to conduct drug combination studies to identify synergistic drug pairs. A library of 500 unapproved drugs was used to perform drug screening in the presence or absence of vemurafenib (at $IC_{20}=6$ μM). The drug library was diluted from 10 mM stock solution to sub-stock solutions of 5, 0.5 and 0.05 mM (1000× final concentration) to give final screening concentrations of 5, 0.5 and 0.05 μM.

30 nL of library drug (at 1000× concentration) was spotted into appropriate wells of a 384 black walled plate (Corning #3712). Duplicate drug-spotted plates were prepared and to them were added Yulac614 cells which were pre-treated with either DMSO (0.01% final) or vemurafenib (6 μM final). The Yulac614 cells were grown in OptiMEM (Life Technologies) containing 5% FBS (Sigma Aldrich F2442-500ML, Lot 12D370) Penicillin/Streptomycin (100×) (CellGro Ref 30-002). 30 uL of cells were dispensed per well using a Multidrop Combi (Thermo Fisher Scientific) to give a final cell density of 2,000 cells per well.

Plates were incubated for 72 h at 37° C. under an atmosphere of 5% $CO_2$ in a humidified incubator. Cell viability was determined with CellTiter-Glo® luminescence assay (Promega) as per the manufacturer's instructions. Viability was expressed as a percentage of control (DMSO)

cells. The viability of the library drug alone was compared to the library drug+vemurafenib and significant combinations were identified.

Figure 1:
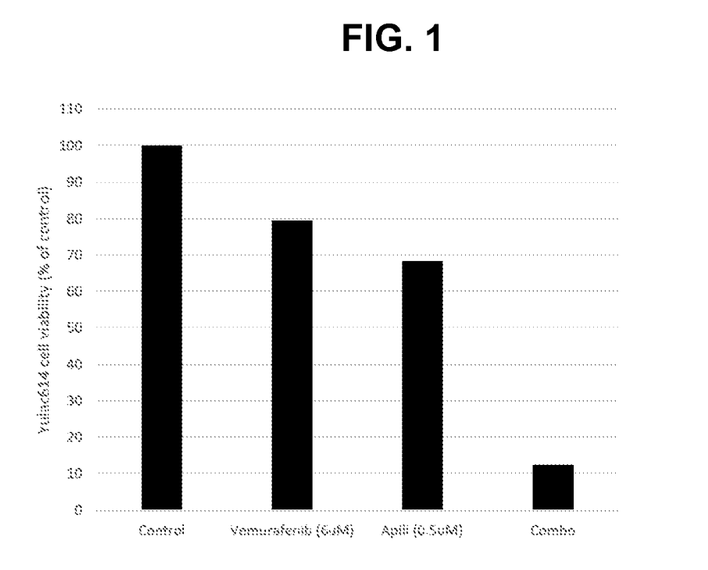
FIG. 1: Screening Yulac614 melanoma cells with a library of 500 unapproved drugs with and without vemurafenib (6 μM) identified apilimod as a drug that when combined with vemurafenib exerts synergistic activity.

Apilimod was identified as an unapproved drug that in combination with vemurafenib significantly reduced Yulac614 cell viability as compared with either drug alone. See FIG. 1.

Figure 2:
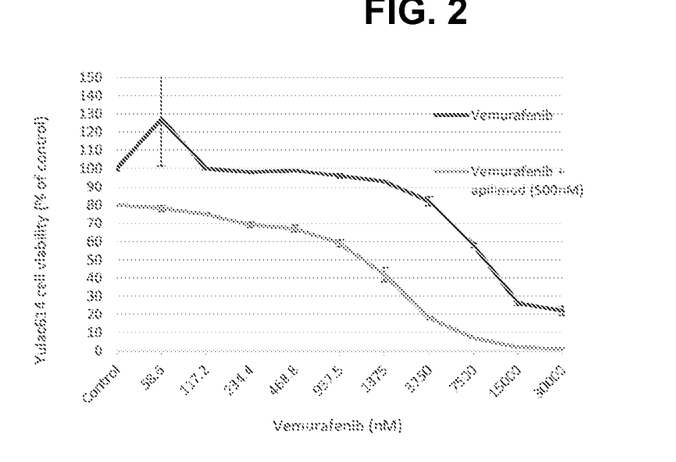
FIG. 2: 10 point concentration response curve of vemurafenib (58.6-30,000 nM) alone (black line) or with apilimod (500 nM) (grey line).

To validate the vemurafenib and apilimod observation, Yulac614 cells were seeded into 96 well plates at a density of 5,000 cells per well in a final volume of 50 uL. Vemurafenib was tested in a 10 point-concentration response curve (58.6-30,000 nM; 2-fold dilutions) in the presence and absence of apilimod (at $IC_{20}$=500 nM). 50 uL of the 10 point drug dilution series (at 2× concentration) was added to the cells. Plates were incubated at 37° C. under an atmosphere of 5% $CO_2$ in a humidified incubator. 72 hours after compound addition relative cell viability was determined by CellTiter-Glo® luminescence assay (Promega) as per the manufacturer's instructions, and values were expressed as a percentage relative to vehicle (DMSO) treated control cells (set to 100%). FIG. 2 depicts a 10 point concentration response curve of vemurafenib (58.6-30,000 nM) alone (black line) or with apilimod (500 nM) (grey line). The results demonstrate that apilimod in combination with vemurafenib is more effective than vemurafenib alone in reducing cell viability of Yulac614 cells.

Figure 3:
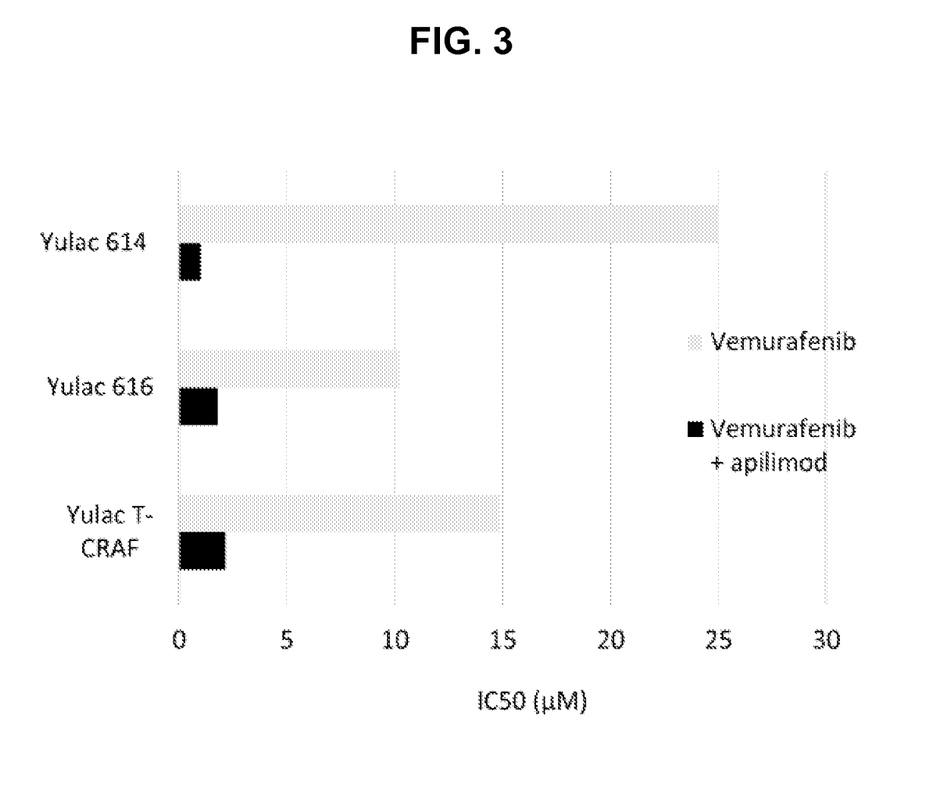
FIG. 3: IC50 values in vemurafenib-resistant cell lines treated with the vemurafenib alone (grey bars) or the combination of vemurafenib and apilimod (black bars).

In another experiment, Yulac (parental-sensitive to vemurafenib), Yulac 614, Yulac 616, Yulac T-CRAF (all resistant to vemurafenib), see Choi et al. 2014) were grown in OptiMEM (Life Technologies) containing 5% FBS (Sigma Aldrich F2442-500ML, Lot 12D370) Penicillin/Streptomycin (100×) (CellGro Ref 30-002). For combination studies, cells were seeded at a density of 5000 cells per well into 96 well plates in a final volume of 50 μL. Cells were treated with apilimod alone (final concentration 13.7-30000 nM; 3-fold dilutions and a total of 8 dilutions), with vemurafenib alone (final concentration 13.7-30000 nM; 3-fold dilutions and a total of 8 dilutions) or the combination of each concentration of apilimod with each concentration of vemurafenib (8×8 matrix). Cells were treated for 72 h before proliferation was assessed using CellTiterGlo® (Promega). For calculation of synergy, CalcuSyn (version 2.11, Biosoft) was used to determine the combination index (CI) as defined by Chou et al. (Chou T C, Talalay P. Quantitative analysis of dose-effect relationships: the combined effects of multiple drugs or enzyme inhibitors. Adv Enzyme Regul 1984; 22:27-55). We constrained the analysis to assess CI values which were within a clinically achievable concentration and also where the fraction effect (Fa) was greater than 0.70 (i.e., a greater than 70% reduction in cell viability with the combination of drugs). Thus, drug combinations producing CI values >1 are antagonistic, CI=1 are additive and CI<1 are synergistic. Using this approach, apilimod was found to act synergistically with vemurafenib in each of these cell lines (see Table 1). The change in sensitivity to vemurafenib by apilimod was determined using GraphPad Prism4 software to calculate IC50 values. As shown in FIG. 3, vemurafenib in combination with apilimod at 370 nM reduced the IC50 by 5.5 to 25 fold compared to vemurafenib alone.

TABLE 1

| Cell line | Vemurafenib/Apilimod concentration (n/M) | Fraction affected | Combination index (CI) |
| --- | --- | --- | --- |
| Yulac (parental) | 1111/370 | 0.74 | 0.3 |
| Yulac614 | 10000/370 | 0.84 | 0.3 |

TABLE 1-continued

| Cell line | Vemurafenib/Apilimod concentration (n/M) | Fraction affected | Combination index (CI) |
| --- | --- | --- | --- |
| Yulac614 | 10000/370 | 0.84 | 0.5 |
| Yulac-CRAF | 10000/370 | 0.84 | 0.2 |

Figure 4:
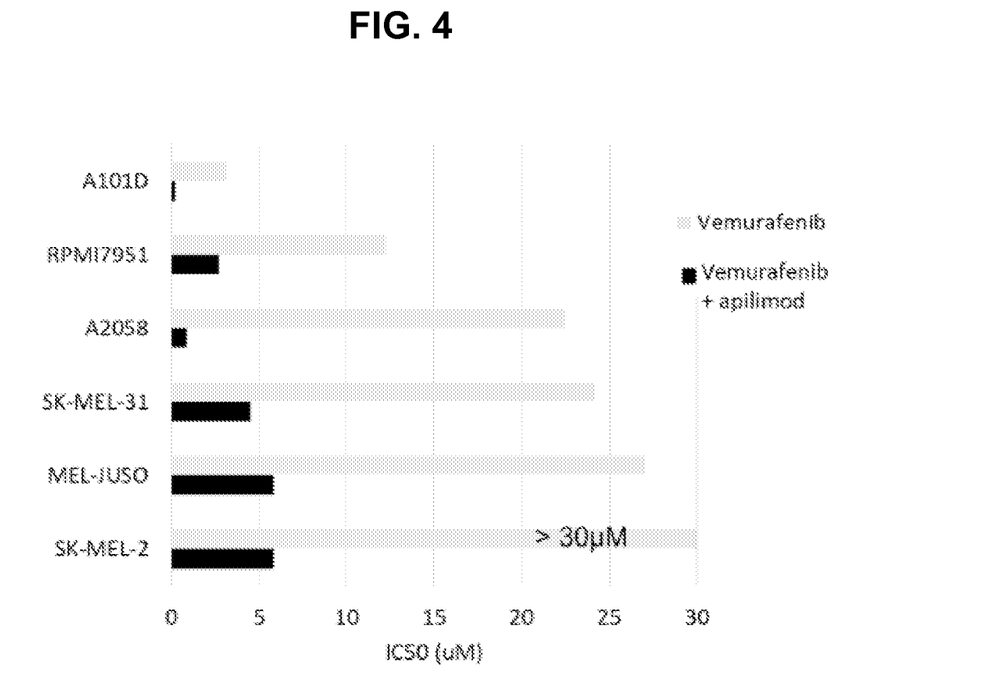
FIG. 4: IC50 values in vemurafenib-resistant cell lines treated with the vemurafenib alone (grey bars) or the combination of vemurafenib and apilimod (black bars).

To extend these findings, a panel of melanoma cell lines that displayed inherent resistance to vemurafenib was chosen for further study with apilimod. A101D, SK-MEL-2, SK-MEL-31, RPMI7951, A2058 (grown in DMEM supplemented with 10% fetal bovine serum) and MEL-JUSO (grown in RPMI supplemented with 10% fetal bovine serum) cells were obtained from ATCC. Cells were seeded at optimal density in 96 well plates in a final volume of 50 μL. Cells were treated with apilimod alone (final 78.1-10000 nM; 2-fold dilutions and a total of 8 dilutions), with vemurafenib alone (final concentration 234-30000 nM; 2-fold dilutions and a total of 8 dilutions) or the combination of each concentration of apilimod with each concentration of vemurafenib (8×8 matrix). Cells were treated for 72 h before proliferation was assessed using CellTiterGlo® (Promega). For calculation of synergy, CalcuSyn (version 2.11, Biosoft) was used to determine the combination index (CI) as described above. Using this approach, apilimod was found to act synergistically with vemurafenib in each cell line (see Table 2). The change in sensitivity to vemurafenib by apilimod was determined using GraphPad Prism4 software to calculate IC50 values. As shown in FIG. 4, vemurafenib in combination with apilimod at 185 nM (A101D, RPMI7951, A2058 and MEL-JUSO cells) or 312 nM (SK-MEL-2 and SK-MEL-31) reduced the IC50 by 4.5 to 25 fold compared to vemurafenib alone.

TABLE 2

| Cell line | Vemurafenib/Apilimod concentration (nM) | Fraction afffected | Combination index (CI) |
| --- | --- | --- | --- |
| RPMI7951 | 3750/185 | 0.71 | 0.18 |
| MEL-JUSO | 7500/185 | 0.78 | 0.05 |
| SK-MEL-2 | 15000/312 | 0.72 | 0.1 |
| SK-MEL-31 | 15000/312 | 0.78 | 0.03 |
| A101D | 7500/185 | 0.91 | 0.11 |
| A2058 | 15000/185 | 0.84 | 0.02 |

Combination index (CI) values for indicated vemurafenib-resistant cell lines treated with the combination of vemurafenib and apilimod. CI values >1 are antagonistic, CI = 1 are additive and CI <1 are synergistic.

What is claimed is:

1. A method for treating melanoma in a subject in need thereof, the method comprising administering to the subject a pharmaceutical composition comprising a therapeutically effective amount of apilimod, or a pharmaceutically acceptable salt thereof, and vemurafenib in a single dosage form with the apilimod, or in a separate dosage form.

2. The method of claim 1, wherein the apilimod is apilimod dimesylate.

3. The method of claim 1, wherein the composition is an oral dosage form or a dosage form suitable for intravenous administration.

4. The method of claim 1, wherein the melanoma is a metastatic or malignant melanoma.

5. A method for treating melanoma in a human subject in need thereof, the method comprising assaying a biological sample of the subject's cancer for one or more mutations in the BRAF protein selected from V600E BRAF and V600K BRAF, or the genetic equivalents thereof, identifying the subject having either of these mutations as a patient for treatment with a combination therapy comprising apilimod and vemurafenib, and administering a combination therapy comprising apilimod and vemurafenib to the subject.

6. The method of claim 1, wherein the melanoma is refractory or non-responsive.

7. The method of claim 1, wherein the vemurafenib is administered in a separate dosage form from the apilimod.

8. A method for treating melanoma in a human subject in need thereof, the method comprising administering to the subject apilimod, or a pharmaceutically acceptable salt thereof, and vemurafenib.

9. The method of claim 8, wherein the vemurafenib is administered in a separate dosage form from the apilimod.

10. The method of claim 8, further comprising determining the presence of one or more of a V600E BRAF protein mutation and a V600K BRAF protein mutation in a biological sample of the subject's cancer.

11. The method of claim 8, wherein the apilimod is apilimod dimesylate.

\* \* \* \* \*